(12) United States Patent
Wieslander et al.

(10) Patent No.: US 12,138,280 B2
(45) Date of Patent: *Nov. 12, 2024

(54) METHOD AND SYSTEM FOR PROVIDING PERITONEAL DIALYSIS FLUIDS WITH VARIABLE POTASSIUM CONCENTRATIONS

(71) Applicant: GAMBRO LUNDIA AB, Lund (SE)

(72) Inventors: Anders Wieslander, Lund (SE); Olof Jansson, Vellinge (SE); Anders Wellings, Bellair Beach, FL (US)

(73) Assignee: GAMBRO LUNDIA AB, Lund (SE)

( * ) Notice: Subject to any disclaimer, the term of this patent is extended or adjusted under 35 U.S.C. 154(b) by 264 days.

This patent is subject to a terminal disclaimer.

(21) Appl. No.: 16/760,569

(22) PCT Filed: Oct. 25, 2018

(86) PCT No.: PCT/EP2018/079244
§ 371 (c)(1),
(2) Date: Apr. 30, 2020

(87) PCT Pub. No.: WO2019/086317
PCT Pub. Date: May 9, 2019

(65) Prior Publication Data
US 2020/0338117 A1 Oct. 29, 2020

Related U.S. Application Data

(60) Provisional application No. 62/581,217, filed on Nov. 3, 2017.

(51) Int. Cl.
*A61K 33/00* (2006.01)
*A61K 9/08* (2006.01)
*A61M 1/28* (2006.01)

(52) U.S. Cl.
CPC ............... *A61K 33/00* (2013.01); *A61K 9/08* (2013.01); *A61M 1/287* (2013.01)

(58) Field of Classification Search
CPC ........... A61K 2300/00; A61K 31/7004; A61K 33/06; A61K 33/14; A61K 9/08; A61K 33/00; A61K 47/02; A61K 47/26; A61M 1/287; A61M 1/03
See application file for complete search history.

(56) References Cited

U.S. PATENT DOCUMENTS

| | | | | |
|---|---|---|---|---|
| 5,344,392 A | * | 9/1994 | Senninger | A61M 1/1656 604/4.01 |
| 6,967,002 B1 | * | 11/2005 | Edgson | A61L 2/0023 422/38 |
| 10,894,119 B2 | * | 1/2021 | Wieslander | A61M 1/287 |
| 2005/0276868 A1 | * | 12/2005 | Degreve | A61K 33/00 424/717 |

FOREIGN PATENT DOCUMENTS

| | | |
|---|---|---|
| CN | 101163469 A | 4/2008 |
| EP | 1753437 A1 | 2/2007 |
| JP | 2000051348 A | 2/2000 |
| JP | 201004231 A | 2/2010 |
| WO | 2006001962 A1 | 1/2006 |
| WO | WO 2017191301 A1 | 11/2017 |

OTHER PUBLICATIONS

International Search Report; International Application No. PCT/EP2018/079245; mailed Jan. 30, 2019; 4 Pages.
Written Opinion of the International Searching Authority; International Application No. PCT/EP2018/079245; mailed Jan. 30, 2019; 6 Pages.
Erixon Martin et al., "How to avoid glucose degradation products in peritoneal dialysis fluids", vol. 26, No. 4, ISSN:0896-8608; Jul. 1, 2006 (Jul. 1, 2006), p. 490-497, Peritoneal Dialysis International, Pergamon Press, New York, NY, US; Retrieved from the Internet: URL:http://www.pdiconnect.com/content/26/4/490.full.pdf+html ; XP008185121; ISSN:0896-8608; 8 Pages.
Office Action for Chinese Patent Application No. 2018800687195 dated Mar. 3, 2023.

* cited by examiner

*Primary Examiner* — Ernst V Arnold
(74) *Attorney, Agent, or Firm* — K&L Gates LLP

(57) ABSTRACT

Methods and systems are provided for preparing a ready-to-use peritoneal dialysis fluid for peritoneal dialysis of a patient having a deficiency in potassium. The methods comprise mixing, immediately before administration to the patient, appropriate amounts of at least a first concentrate, a second concentrate, and a third concentrate with an appropriate amount of water to form a ready-to-use dialysis fluid. The first concentrate comprises glucose, has a pH of between 1.5 and 4, and is free of potassium ions; the second concentrate comprises a physiologically acceptable buffer and is free of potassium ions; and the third concentrate comprises the physiologically acceptable buffer and potassium ions.

24 Claims, 1 Drawing Sheet

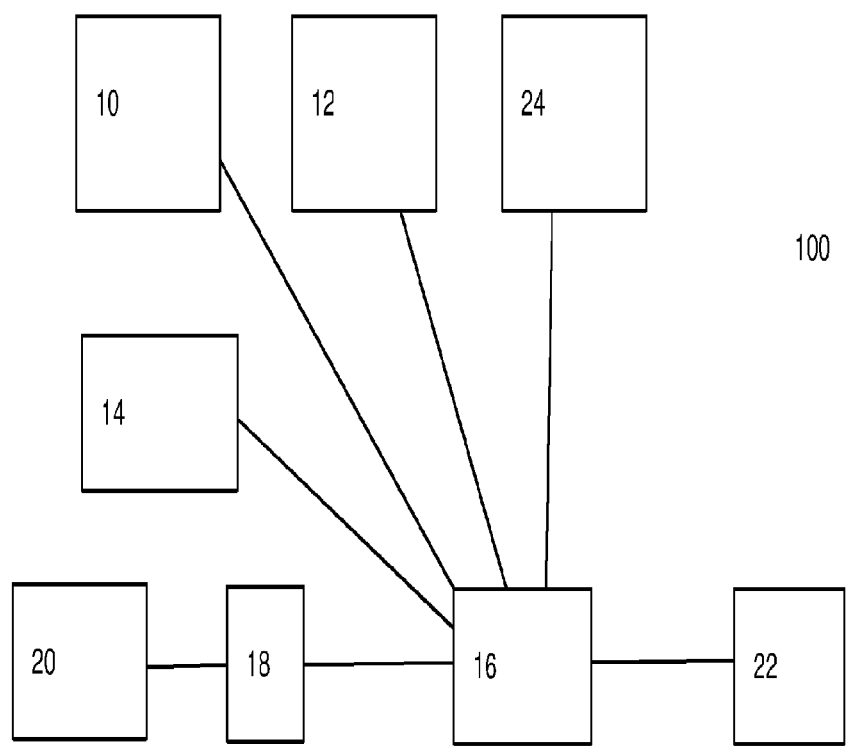

METHOD AND SYSTEM FOR PROVIDING PERITONEAL DIALYSIS FLUIDS WITH VARIABLE POTASSIUM CONCENTRATIONS

PRIORITY CLAIM

The present application is a National Phase of International Application No. PCT/EP2018/079244, filed Oct. 25, 2018, which claims priority to U.S. Provisional Patent Application No. 62/581,217, filed Nov. 3, 2017, the entire contents of each of which are incorporated herein by reference and relied upon.

BACKGROUND

Field

The disclosure relates to the field of fluid compounding for preparing fluids particularly for the treatment of renal insufficiency. More specifically, it relates to a method for compounding finished fluids from three or more concentrates for use as a dialysis fluid for the treatment of renal insufficiency. In particular, the methods may be used for preparing fluids for peritoneal dialysis, particularly for preparing fluids at the point-of-care of the patient.

Description of the Related Art

Patients with acute or chronic renal insufficiency may need supporting treatment in the form of dialysis for the removal of waste substances and excess of fluid from the body. Dialysis is a process to remove fluid and waste products from the patient by the use of diffusion or convective transport. Various dialysis techniques with associated dialysis fluids may be differentiated. Which dialysis technique to use depends on the patient needs, treatment demands and available resources.

Peritoneal dialysis is one available dialysis technique for patients having renal failure. During this treatment, a sterile peritoneal dialysis fluid is infused in the peritoneal cavity of the patient via a catheter inserted through the abdominal wall. In peritoneal dialysis, the peritoneal membrane serves as the dialysis membrane. An osmotic pressure gradient is applied by the addition of an osmotic agent to the dialysis fluid which will cause fluid removal from the blood. The amount of fluid removed during the dialysis treatment depends on the concentration of the osmotic agent chosen in the fluids used; the higher concentration, the larger amount of fluid is removed. Methods of peritoneal dialysis treatment include, for example, Continuous Ambulatory Peritoneal dialysis (CAPD), Continuous Flow Peritoneal Dialysis (CFPD), Intermittent Peritoneal Dialysis (IPD), Tidal Peritoneal Dialysis (TPD) and Automated Peritoneal Dialysis (APD).

In automated peritoneal dialysis, an automated cycler is used to infuse and drain dialysis fluid. This form of treatment may be done, for example, automatically at night while the patient sleeps, but can of course also be performed at other times of the day. The cycler measures the amount of fluid infused and the amount removed to compute the net fluid removal. The treatment sequence usually begins with an initial drain cycle to empty the peritoneal cavity of dialysate (also called spent dialysis fluid). The cycler then performs a series of fill, dwell, and drain cycles, typically finishing with a fill cycle.

Peritoneal dialysis generally requires large volumes of dialysis fluids. Generally, at each application, or exchange, a given patient will infuse 0.5 to 3 liters of dialysis fluid into the peritoneal cavity. The fluid is allowed to dwell for approximately 1-4 hours, at which time it is drained out and exchanged for fresh fluid. Generally, four such exchanges are performed daily. Approximately 8 to 20 liters of dialysis fluid is required per day, 7 days a week, and 365 days a year for each patient.

The peritoneal dialysis fluids have traditionally been provided in bags, often as 1.5 L, 2 L, 3 L, 5 L, or 6 L bags, and being terminally sterilized. Shipping and storage of the sheer volume of fluids required is both tremendously inconvenient and expensive. Further, for the patient, the repeated connection and disconnection of multiple fluid containers creates a risk of microbiological contamination at the point of connection. Additionally, large amounts of waste material, in form of empty containers and packaging, and their proper disposal are increasingly becoming a concern.

Further, patients receiving peritoneal dialysis may develop hypokalemia (low potassium levels in the blood) caused by multiple factors such as malnutrition and gastrointestinal losses. Potassium is a mineral needed to keep the nerves, muscles, and heart working well. Low or high potassium can cause irregular heartbeats and may even cause the heart to stop beating. Eating more potassium-rich foods often does not maintain potassium levels in a normal range, and both intravenous and oral routes for potassium repletion have disadvantages. Merely adding potassium to ready-to-use peritoneal dialysis fluid bags increases costs and does not provide flexibility to patients in the range of possible potassium concentrations because the number of different peritoneal dialysis fluid bags available in the market already is high, with various dialysis fluid bags having, for example, different glucose concentrations, different calcium concentrations, different lactate concentrations, and/or different bicarbonate concentrations.

A need therefore exists for an improved method and system for delivering potassium to peritoneal dialysis patients.

SUMMARY

The disclosure provides a method for preparing a ready-to-use peritoneal dialysis fluid for treating a dialysis patient having a deficiency in potassium. The methods have flexibility and capability to provide ready-to-use peritoneal dialysis fluids having various potassium concentrations. Further, the methods disclosed herein avoid the problems of shipping and storing large volumes of ready-to-use dialysis fluids. In particular, the disclosure provides methods wherein small volumes of concentrated dialysis fluids are combined and diluted with purified water at the point of care, e.g., close to the patient. A first concentrate comprises glucose, allowing different volumes of glucose to be dosed to obtain different glucose concentrations. A second concentrate comprises a physiologically acceptable buffer and is free of potassium ions. A third concentrate comprises the physiologically acceptable buffer and potassium ions, allowing different volumes of potassium to be dosed to obtain different potassium concentrations.

In one embodiment, the method comprises mixing, immediately before administration to the patient, appropriate amounts of at least a first concentrate, a second concentrate, and a third concentrate with an appropriate amount of water to form a ready-to-use dialysis fluid; wherein the first concentrate comprises glucose, has a pH of between 1.5 and 4, low levels of glucose degradation products and is free of potassium ions; the second concentrate comprises a physiologically acceptable buffer and is free of potassium ions; and the third concentrate comprises the physiologically acceptable buffer and potassium ions.

In one embodiment, which may be combined with any of the embodiments disclosed herein unless specified otherwise, the second concentrate and/or the third concentrate has a pH of between 5.0 and 9.0.

In one embodiment, which may be combined with any of the embodiments disclosed herein unless specified otherwise, the physiologically acceptable buffer is selected from the group consisting of acetate, lactate, citrate, pyruvate, carbonate, bicarbonate, amino acid buffers, and mixtures thereof. For example, the physiologically acceptable buffer may comprise lactate, bicarbonate, or a mixture thereof.

In one embodiment, which may be combined with any of the embodiments disclosed herein unless specified otherwise, the second concentrate and/or the third concentrate further comprises at least one electrolyte selected from the group consisting of sodium, calcium, and magnesium.

In one embodiment, which may be combined with any of the embodiments disclosed herein unless specified otherwise, exclusive of the potassium ions, the third concentrate is the same as the second concentrate.

In one embodiment, which may be combined with any of the embodiments disclosed herein unless specified otherwise, the first concentrate, the second concentrate and/or the third concentrate is configured to be used for dilutions of between 1:10 and 1:50.

In one embodiment, which may be combined with any of the embodiments disclosed herein unless specified otherwise, the water is sterile water produced by reverse osmosis and sterile filtration.

In one embodiment, which may be combined with any of the embodiments disclosed herein unless specified otherwise, the ready-to-use dialysis fluid has a potassium ion concentration of about 0.1 mM to about 4 mM. According to another embodiment, which may be combined with any of the embodiments disclosed herein unless specified otherwise, the ready-to-use dialysis fluid has a potassium ion concentration of about 0.5 mM to about 4 mM.

In one embodiment, which may be combined with any of the embodiments disclosed herein unless specified otherwise, the ready-to-use dialysis fluid contains: 90-140 mM sodium ($Na^+$), 0.1-4 mM potassium ($K^+$), 0-2 mM calcium ($Ca^{2+}$), 0-0.75 mM magnesium ($Mg^{2+}$), 0-40 mM lactate, 0-40 mM bicarbonate, and 0-5% glucose. In another embodiment, which may be combined with any of the embodiments disclosed herein unless specified otherwise, the ready-to-use dialysis fluid contains: 90-140 mM sodium ($Na^+$), 0.5-4 mM potassium ($K^+$), 0-2 mM calcium ($Ca^{2+}$), 0-0.75 mM magnesium ($Mg^{2+}$), 0-40 mM lactate, 0-40 mM bicarbonate, and 0-5% glucose.

In one embodiment, which may be combined with any of the embodiments disclosed herein unless specified otherwise, the ready-to-use dialysis fluid contains: 132 mM sodium ($Na^+$), 1-4 mM potassium ($K^+$), 0.5-2 mM calcium ($Ca^{2+}$), 0.25-0.75 mM magnesium ($Mg^{2+}$), 0-40 mM lactate, and 0-5% glucose.

In one embodiment, which may be combined with any of the embodiments disclosed herein unless specified otherwise, the ready-to-use dialysis fluid contains 15 mM to 40 mM lactate.

In one embodiment, which may be combined with any of the embodiments disclosed herein unless specified otherwise, the first concentrate further comprises an acid selected from HCl and organic acids.

In one embodiment, which may be combined with any of the embodiments disclosed herein unless specified otherwise, the ready-to-use dialysis fluid is used for automated peritoneal dialysis (APD).

In one embodiment, which may be combined with any of the embodiments disclosed herein unless specified otherwise, the first concentrate comprises 25-60% glucose.

In one embodiment, which may be combined with any of the embodiments disclosed herein unless specified otherwise, the second concentrate comprises: 1.0-5.5 M sodium ($Na^+$), 0-0.15 M calcium ($Ca^{2+}$), 0-0.03 M magnesium ($Mg^{2+}$), 0-1.6 M lactate, and 0-1.6 M bicarbonate.

In one embodiment, which may be combined with any of the embodiments disclosed herein unless specified otherwise, the third concentrate comprises: 1.0-5.5 M sodium ($Na^+$), 0-0.15 M calcium ($Ca^{2+}$), 0-0.03 M magnesium ($Mg^{2+}$), 0.04-0.1 M potassium ($K^+$), 0-1.6 M lactate, and 0-1.6 M bicarbonate.

In one embodiment, which may be combined with any of the embodiments disclosed herein unless specified otherwise, the ready-to-use dialysis fluid is prepared using a system comprising: a) a proportioning device or peritoneal dialysis cycler operating a disposable pump and valve set; b) at least one source of water adapted for connection with said disposable pump and valve set operated by the proportioning device; c) at least one source of the first concentrate adapted for connection with said disposable pump and valve set; d) at least one source of the second concentrate adapted for connection with said disposable pump and valve set; and e) at least one source of the third concentrate adapted for connection with said disposable pump and valve set. Of course, the principle of the invention can also be put into practice with a different machine and process, as long as the ready-to-use solution is generated from at least one source of the first concentrate, at least one source of the second concentrate and at least one source of the third concentrate.

In one embodiment, which may be combined with any of the embodiments disclosed herein unless specified otherwise, a proportioning device includes a controller programmed to cause the proportioning device to perform multiple fills using the ready-to-use dialysis fluid as a patient fill solution, wherein (i) the fill solutions of each patient fill contain the third concentrate, (ii) the fill solutions of less than all patient fills contain the third concentrate, (iii) the fill solutions of each patient fill contain a like, or substantially like, amount or concentration of the third concentrate, and/or (iv) one or more or all of the fill solutions of the multiple patient fills contain a different amount or concentration of the third concentrate.

In one embodiment, which may be combined with any of the embodiments disclosed herein unless specified otherwise, the method of preparing a ready-to-use peritoneal dialysis fluid for peritoneal dialysis of a patient having a deficiency in potassium comprises mixing, immediately before administration to the patient, appropriate amounts of at least a first concentrate, a second concentrate, and a third concentrate with an appropriate amount of water to form a ready-to-use dialysis fluid. The first and second concentrates are both free of potassium ions and the third concentrate comprises potassium ions.

In one embodiment, which may be combined with any of the embodiments disclosed herein unless specified otherwise, the peritoneal dialysis fluid comprises 0.1-4 mM potassium. In another embodiment, which may be combined with any of the embodiments disclosed herein unless specified otherwise, the peritoneal dialysis fluid comprises 0.5-4 mM potassium.

In one embodiment, which may be combined with any of the embodiments disclosed herein unless specified otherwise, systems for administering peritoneal dialysis fluid to a patient having a deficiency in potassium are provided. The system comprises (i) a proportioning device, (ii) at t least one source of water adapted for operation with said proportioning device, (iii) t least one source of the first concentrate comprising glucose and free of potassium ions with a pH of 1.5 to 4.5 adapted for operation with the proportioning device, (iv) at least one source of the second concentrate comprising a physiologically acceptable buffer and is free of potassium ions adapted for operation with the proportioning device, and (v) at least one source of the third concentrate comprising a physiologically acceptable buffer and potassium ions adapted for operation with said proportioning device.

BRIEF DESCRIPTION OF THE DRAWINGS

FIG. 1 provides scheme 100 showing a system for preparing a ready to use peritoneal dialysis fluid. A container 10 comprising a first concentrate, a container 12 comprising a second concentrate, and container 24 comprising a third concentrate are each connected to a proportioning device 16 or cycler for mixing by conduits. A source 14 of purified water is also connected to a mixer, which may be part of a disposable pump and valve set operated by proportioning device or cycler 16, by a conduit. The proportioning device or cycler 16 is controlled by a controller 18 based on input from a user interface 20. Depending on such user input and control signals from the controller 18, the proportioning device 16 receives specific amounts of first, second, and third concentrates, as well as water, from said sources 10, 12, 24, and 14, and produces a ready-to-use peritoneal dialysis fluid that is delivered through output/container 22.

DETAILED DESCRIPTION

Definitions

The term "first concentrate" means herein the source of glucose. The source may be provided as fluid concentrate.

The term "second concentrate" means herein the source of physiologically acceptable buffer. Examples of physiologically acceptable buffers are acetate, lactate, citrate, pyruvate, carbonate, bicarbonate, and amino acid buffer, if not otherwise specified. Further, the buffers are intended to be in form of alkali, for example alkali lactate, and alkali bicarbonate, such as sodium lactate, and sodium bicarbonate.

The term "third concentrate" means herein a source of physiologically acceptable buffer as defined for "the second concentrate" and additionally comprising potassium.

The term "lactate" means lactic acid or any salt thereof. For example, the salt may be formed with sodium, calcium, or magnesium.

The term "terminal sterilized" is herein intended to mean that the product is sterilized in its final package. The terminal sterilization may include heat sterilization and/or radiation sterilization, but is preferably heat sterilized in an autoclave at a temperature of at least 100° C., preferably at least 121° C.

The term "dilution" as used herein refers to the mixing of a small, measured sample with a large volume of, for example, sterile water, saline or other appropriate liquid called the diluent or a dilution blank. A single dilution is calculated as follows:

Dilution=volume of the sample/(total volume of the sample+diluent volume).

For example, the dilution of 1 mL into 9 mL equals: 1/1+9, which is the same as 1/10 which is written 1/10 or $10^{-1}$. This can then be called a one to ten dilution.

Peritoneal Dialysis Fluids

The disclosure provides methods for preparing a ready-to-use peritoneal dialysis fluid for peritoneal dialysis of a patient having a deficiency in potassium. The methods comprise: mixing using the cycler 16 illustrated in FIG. 1, immediately before administration to the patient, appropriate amounts of at least a first concentrate, a second concentrate, and a third concentrate with an appropriate amount of water to form a ready-to-use dialysis fluid. In an embodiment, the ready-to-use peritoneal dialysis fluid may be used for automated peritoneal dialysis (APD).

In the disclosed methods, the first concentrate comprises glucose and is free of potassium ions. The first concentrate has a pH of between 1.5 and 4.5. For example, the pH is between 1.5 and 3, between 2 and 3.5, between 2.2 and 3.2, between 2.5 and 3.2, between 2.2 and 2.8, or between 2.4 and 2.8. The concentrate is acidified by, for example, addition of hydrochloric acid (HCl) or an organic acid. Examples of organic acids are citric acid and acetic acid. The concentrate may comprise 25-60% glucose, for example 25-40%, 30-50%, or 40-60%. Advantageously, using a concentrate comprising glucose provides great flexibility in the concentration of glucose obtained for the ready-to-use fluid. In some cases, the first concentrate is free of sodium ions, which provides greater flexibility to adjust the glucose concentration of the ready-to-use fluid without affecting the sodium concentration. In the disclosed methods, the second concentrate comprises a physiologically acceptable buffer and is free of potassium ions. Suitable buffers include, but are not limited to, acetate, lactate, citrate, pyruvate, carbonate, bicarbonate, amino acid buffers (e.g., histidine), and mixtures thereof. For example, the buffer comprises lactate, bicarbonate, or a mixture thereof. The second concentrate typically has a pH of between 5.5 and 9, for example between 5.5 and 8.5, between 6.5 and 9, between 6 and 8.5, between 6.5 and 8.0, or between 6.5 and 7.5. The second concentrate optionally comprises one or more electrolytes. Suitable electrolytes include, but are not limited to, sodium, calcium, and magnesium. A second concentrate as disclosed herein may have the following content:

| | |
|---|---|
| sodium (Na$^+$) | 1-5.5M, for example, 2-4M, or 3-4M, or 2.6M |
| calcium (Ca$^{2+}$) | 0-0.15M, for example, 0-0.12M, or 0.05-0.1M, or 0.025M |
| magnesium (Mg$^{2+}$) | 0-0.03M, for example, 0.01-0.02M, or 0.005M |
| lactate | 0-1.6M, for example, 0.5-1M, or 0.8M |
| bicarbonate | 0-1.6M, for example, 0.5-1M |

In the disclosed methods, the third concentrate comprises the physiologically acceptable buffer and potassium ions. Suitable buffers include, but are not limited to, acetate, lactate, citrate, pyruvate, carbonate, bicarbonate, amino acid buffers (e.g., histidine), and mixtures thereof. For example, the buffer comprises lactate, bicarbonate, or a mixture thereof. The second concentrate typically has a pH of between 5.5 and 9, for example between 5.5 and 8.5, between 6.5 and 9, between 6 and 8.5, between 6.5 and 8.0, or between 6.5 and 7.5. The third concentrate optionally comprises one or more additional electrolytes. Suitable electrolytes include, but are not limited to, sodium, calcium, and magnesium. A third concentrate as disclosed herein may have the following content:

| | |
|---|---|
| sodium (Na$^+$) | 1-5.5M, for example, 2-4M, or 3-4M |
| calcium (Ca$^{2+}$) | 0-0.15M, for example, 0-0.12M, or 0.05-0.1M |
| magnesium (Mg$^{2+}$) | 0-0.03M, for example, 0.01-0.02M |
| potassium (K$^+$) | 0.04-0.1M |
| lactate | 0-1.6M, for example, 0.5-1M |
| bicarbonate | 0-1.6M, for example, 0.5-1M |

The third concentrate, exclusive of the potassium ions, generally is the same as the second concentrate. As used herein, the "same" means that the third concentrate (1) includes each of the electrolytes and buffers included in the second concentrate; (2) includes those electrolytes and buffers in a concentration within ±0.5 M, for example, ±0.3 M, ±0.2 M, ±0.1 M, or ±0.05 M of the concentration in the second concentrate; and (3) has a pH within ±0.3 pH units, for example, ±0.2, ±0.1, or ±0.05 pH units of the pH of the second concentrate. Using second and third concentrates comprising the same electrolytes and buffers, at the same concentrations, and having the same pH advantageously provides methods wherein great flexibility in the concentration of potassium is achieved, without affecting the relative amounts of other electrolytes and buffers in the concentrates.

The first concentrate, the second concentrate and/or the third concentrate may be configured to be used for dilutions of between 1:10 and 1:50 to obtain the ready-to-use peritoneal dialysis solution. For example, the first, second, or third concentrate may be configured to be used for dilutions of between 1:15 and 1:35, between 1:20 and 1:30, or between 1:25 and 1:30, based on the total volume of the ready-to-use dialysis fluid. The level of concentrate also is referred to as 10×, 15×, 20×, 25×, 30×, 35×, 40× and 50×. The concentrates of components for preparing the ready-to-use peritoneal dialysis fluid may each be provided in volumes of about 0.5 L to about 5 L, for example, about 1 L to about 3 L or about 1 L to about 2 L. Advantageously, these concentrates having smaller volumes will replace the 8-55 L of peritoneal dialysis fluid typically used by patients.

The pH of the ready-to-use peritoneal dialysis fluids disclosed herein typically is between 5-8, for example between 6.5-7.5, or between 6.8-7.5, or between 6.0-8.5. The ready-to-use peritoneal dialysis fluids typically have a pH close to physiological/neutral to reduce infusion pain.

The potassium ion concentration of the ready-to-use peritoneal dialysis fluids disclosed herein typically is about 0.5 to about 4 mM, for example, about 1 to about 4 mM, about 1.6 to about 4 mM, about 1.6 to about 3 mM, or about 1.6 to about 2 mM.

The lactate concentration of the ready-to-use peritoneal dialysis fluids disclosed herein typically is about 0 mM to about 40 mM, about 10 mM to about 40 mM, about 15 mM to about 40 mM, about 20 mM to about 40 mM, about 30 mM to about 40 mM, or about 35 mM to about 40 mM.

A ready-to-use peritoneal dialysis solution as disclosed herein may have the following content:

| | |
|---|---|
| sodium (Na$^+$) | 90-140 mM, for example, 100-140 mM, 110-140 mM, 115-125 mM, 115-132 mM, 120-140 mM, 125-135 mM, 129-135 mM, or 132 mM |
| potassium (K$^+$) | 0.1-4 mM, for example, 0.5-4 mM, 1-4 mM, 1.6-4 mM, 1.6-3 mM, or 1.6-2 mM |
| calcium (Ca$^{2+}$) | 0-2 mM, for example, 0.5-2 mM, 1-2 mM, 1-1.75 mM, or 1.25-1.5 mM |
| magnesium (Mg$^{2+}$) | 0-0.75 mM, for example, 0.1-0.75 mM, 0.25-0.75 mM, 0.25-0.5 mM, 0.3-0.45 mM, or 0.35-0.4 |
| lactate | 0-40 mM, for example, 10-40 mM, 15-40 mM, 20-40 mM, 30-40 mM, or 35-40 mM |
| bicarbonate | 0-40 mM, for example, 10-40 mM, 15-40 mM, 20-40 mM, 25-40 mM, 30-40 mM, or 35-40 mM |
| glucose | 0-5%, for example, 0.5-5%, 1-2%, 1-5%, 1.5-5%, 2-5%, 2-3%, or 3-5% |

A ready-to-use peritoneal dialysis solution as disclosed herein may have the following content:

| | |
|---|---|
| sodium (Na$^+$) | 90-140 mM |
| potassium (K$^+$) | 0.1-4 mM |
| calcium (Ca$^{2+}$) | 0-2 mM |
| magnesium (Mg$^{2+}$) | 0-0.75 mM |
| lactate | 0-40 mM |
| bicarbonate | 0-40 mM |
| glucose | 0-5% |

A ready-to-use peritoneal dialysis solution as disclosed herein may have the following content:

| | |
|---|---|
| sodium (Na$^+$) | 132 mM |
| potassium (K$^+$) | 1-4 mM |
| calcium (Ca$^{2+}$) | 0.5-2 mM |
| magnesium (Mg$^{2+}$) | 0.25-0.75 mM |
| lactate | 0-40 mM |
| glucose | 1.3-5% |

The list of examples of ready-to-use peritoneal dialysis fluids is not exhaustive or intended to limit the present invention.

The system for preparing a ready-to-use peritoneal dialysis solution as disclosed herein may comprise the following: a) a proportioning device or cycler operating a disposable pump and valve set; b) at least one source of water adapted for connection with said disposable pump and valve set operated by the proportioning device or cycler; c) at least one source of the first concentrate adapted for connection with a) and b); d) at least one source of the second concentrate adapted for connection with a) and b); and e) at least one source of the third concentrate adapted for connection with a) and b).

The system as is described herein comprises a proportioning device or cycler. In the proportioning device are the concentrates admixed, i.e. proportioned and compounded, to form a ready-to-use peritoneal dialysis fluid. With the system as defined herein there is provided a ready way to prepare the dialysis fluid for the peritoneal dialysis treatment. Less amount and less volumes of concentrates are to be handled in connection with the treatment of the patient.

Systems for peritoneal dialysis and/or proportioning devices also are described in International Application Nos. PCT/US2017/031396, PCT/EP2017/060769, WO 2013/1141896, WO 2012/129501, U.S. application Ser. Nos. 15/588,220, 15/588,235, 15/588,454, and U.S. Pat. No. 5,344,392 which are incorporated herein by reference in their entireties. Commercially available proportioning devices or cyclers include, for example, an AMIA® APD machine (Baxter International Inc.).

The system for preparing a ready-to-use peritoneal dialysis solution as disclosed herein includes at least one water source. The water to be added to the concentrate(s) included in this production shall have a certain chemical and microbiological quality (defined in e.g. European Pharmacopoeia) suitable for its application.

Water to be included in the source of water should be within limits that are safe from a microbiological and chemical perspective; this water could for example be "purified water", "highly purified water", "ultrapure water", "water for injection" (WFI), "sterile WFI", "water for hemodialysis", "distilled water", "sterile purified water" and "water for pharmaceutical use". For example, the water to be included in the source of water may be sterile water produced by reverse osmosis and/or sterile filtration.

The herein defined first concentrate, second concentrate, and third concentrate may be terminal sterilized before they are included in the system. By having sterilized concentrate, by for example terminal sterilization, included in the system these can be mixed with the water having the quality as defined above and a ready-to-use peritoneal dialysis fluid of high quality is provided. There is no requirement of sterilization of the ready-to-use peritoneal dialysis fluid prepared is such way as the method yields a sterile ready to use final product. By the invention, it is possible to provide the ready-to-use peritoneal dialysis fluid close to the point of care.

FIG. 1 illustrates a system 100 for preparing a ready-to-use peritoneal dialysis fluid. A container 10 comprising a first concentrate, a container 12 comprising a second concentrate, and a container 24 comprising a third concentrate are each connected to a disposable pump and valve set operated by a proportioning device or cycler 16 for mixing by conduits. A source 14 of purified water is also connected to the disposable pump and valve set operated by the proportioning device or cycler 16 by a conduit. The proportioning device or cycler 16 is controlled by a controller 18 based on input from a user interface 20. Depending on such user input and control signals from the controller 18, the proportioning device 16 receives specific amounts of first, second, and third concentrates, as well as water, from sources 10, 12, 24, and 14, and produces a ready-to-use peritoneal dialysis fluid that is delivered through output/container 22.

Proportioning device or cycler 16 under control of controller 18 is in various embodiments configured or programmed to perform multiple drain, fill and dwell cycles (if the patient is initially full with a previous treatment's last fill or midday exchange) or multiple fill, dwell and drain cycles (if the patient starts treatment empty). In either case, it is contemplated to infuse any of the potassium containing concentrates described herein according to a device prescription prepared by a doctor or clinician, wherein: (i) all patient fill solutions contain potassium, (ii) less than all patient fill solutions contain potassium, (iii) each patient fill solution containing potassium contains a like, or substantially like, amount or concentration of potassium, and/or (iv) one or more or all of the patient fill solutions containing potassium contain a different amount or concentration of potassium.

In some embodiments, the second concentrate comprises the following composition:
11.34 g/100 ml NaCl (Mw=58.44 g/mol); 1940 mM
7.84 g/100 ml sodium lactate (Mw=112.06 g/mol); 700 mM
514 mg/100 ml calcium chloride (Mw (CaCl$_2$*2H$_2$O)= 147.01 g/mol); 35.0 mM
304 mg/100 ml magnesium chloride (Mw (hexahydrate) =203.31 g/mol); 14.95 mM, with a pH of approximately 6.4.

In other embodiments, the second concentrate does not comprise the above composition.

While the invention has been described in connection with what is presently considered to be the most practical embodiments, it is to be understood that the invention is not to be limited to the disclosed embodiments, but on the contrary, is intended to cover various modifications and equivalents included within the spirit and the scope of the appended claims.

The invention claimed is:

1. A method for preparing a ready-to-use peritoneal dialysis fluid for peritoneal dialysis of a patient having a deficiency in potassium, the method comprising:
mixing, before administration to the patient, appropriate amounts of at least a first concentrate, a second concentrate, and a third concentrate with an appropriate amount of water to form the ready-to-use peritoneal dialysis fluid,
wherein the first concentrate includes glucose, has a pH of between 1.5 and 4.5, and is free of potassium ions,
wherein the second concentrate includes a physiologically acceptable buffer and is free of potassium ions,
wherein the third concentrate includes the physiologically acceptable buffer and potassium ions, and the potassium ions in the third concentrate have a concentration between 0.04 M and 0.1 M, and
wherein the ready-to-use peritoneal dialysis fluid is a dilution of between 1:10 and 1:50 of at least one of the first concentrate, the second concentrate or the third concentrate, and
wherein exclusive of the potassium ions, the third concentrate is the same as the second concentrate.

2. The method of claim 1, wherein the second concentrate or the third concentrate has a pH of between 5.0 and 9.0.

3. The method of claim 1, wherein the physiologically acceptable buffer includes one or more selected from the group consisting of: acetate, lactate, citrate, pyruvate, carbonate, bicarbonate, and amino acid buffers.

4. The method of claim 1, wherein the physiologically acceptable buffer includes one or both of lactate and bicarbonate.

5. The method of claim 1, wherein the second concentrate or the third concentrate further includes at least one electrolyte selected from the group consisting of sodium, calcium, and magnesium.

6. The method of claim 1, wherein the water is sterile water produced by reverse osmosis or distillation and sterile filtration.

7. The method of claim 1, wherein the ready-to-use dialysis fluid has a potassium ion concentration of about 0.1 mM to about 4 mM.

8. The method of claim 1, wherein the ready-to-use peritoneal dialysis fluid includes:
90 to 140 mM sodium (Na$^+$),
0.5 to 4 mM potassium (K$^+$),
0 to 2 mM calcium (Ca$^{2+}$),
0 to 0.75 mM magnesium (Mg$^{2+}$),
0 to 40 mM lactate,
0 to 40 mM bicarbonate, and
0 to 5% glucose.

9. The method of claim 1, wherein the ready-to-use peritoneal dialysis fluid includes:
132 mM sodium (Na$^+$),
1 to 4 mM potassium (K$^+$), 0.5 to 2 mM calcium ($Ca^{2+}$),
0.25 to 0.75 mM magnesium ($Mg^{2+}$),
0 to 40 mM lactate, and
1 to 5% glucose.

10. The method of claim 1, wherein the ready-to-use peritoneal dialysis fluid contains 15 mM to 40 mM lactate.

11. The method of claim 1, wherein the first concentrate includes an acid selected from HCl and organic acids.

12. The method of claim 1, wherein the ready-to-use peritoneal dialysis fluid is adapted for automated peritoneal dialysis.

13. The method of claim 1, wherein the first concentrate includes 25 to 60% glucose.

14. The method of claim 1, wherein the second concentrate includes:
1.0 to 5.5 M sodium ($Na^+$),
0 to 0.15 M calcium ($Ca^{2+}$),
0 to 0.03 M magnesium ($Mg^{2+}$),
0 to 1.60 M lactate, and
0 to 1.60 M bicarbonate.

15. The method of claim 1, wherein the third concentrate includes:
1.0 to 5.5 M sodium ($Na^+$),
0 to 0.15 M calcium ($Ca^{2+}$),
0 to 0.03 M magnesium ($Mg^{2+}$),
0 to 1.6 M lactate, and
0 to 1.6 M bicarbonate.

16. The method of claim 1, wherein the ready-to-use peritoneal dialysis fluid is prepared using a system including:
a proportioning device;
at least one source of water adapted for operation with the proportioning device;
at least one source of the first concentrate adapted for operation with the proportioning device;
at least one source of the second concentrate adapted for operation with the proportioning device; and
at least one source of the third concentrate adapted for operation with the proportioning device.

17. The method of claim 16, wherein the proportioning device includes a controller programmed to cause the proportioning device to perform multiple fills using the ready-to-use dialysis fluid as a patient fill solution, wherein the controller is programmed to effect at least one from the group consisting of: (i) the patient fill solutions of each fill contain the third concentrate, (ii) the patient fill solutions of less than all fills contain the third concentrate, (iii) the patient fill solutions of each fill contain an amount or concentration of the third concentrate, and (iv) one or more or all of the patient fill solutions of the multiple fills contain a different amount or concentration of the third concentrate.

18. The method of claim 1, wherein the mixing occurs immediately before administration to the patient.

19. A method for preparing a ready-to-use peritoneal dialysis fluid for peritoneal dialysis of a patient having a deficiency in potassium, the method comprising:
mixing, before administration to the patient, appropriate amounts of at least a first concentrate, a second concentrate, and a third concentrate, with an appropriate amount of water, to form the ready-to-use peritoneal dialysis fluid,
wherein the first concentrate is free of potassium ions,
wherein the second concentrate is free of potassium ions,
wherein the third concentrate comprises potassium ions, and the potassium ions in the third concentrate have a concentration between 0.04 M and 0.1 M, and
wherein the ready-to-use peritoneal dialysis fluid is a dilution of between 1:10 and 1:50 of at least one of the first concentrate, the second concentrate or the third concentrate, and
wherein exclusive of the potassium ions, the third concentrate is the same as the second concentrate.

20. The method of claim 19, wherein the ready-to-use peritoneal dialysis fluid includes 0.1 to 4 mM potassium.

21. The method of claim 19, wherein the mixing occurs immediately before administration to the patient.

22. A peritoneal dialysis system for administering a peritoneal dialysis fluid to a patient having a deficiency in potassium, the system comprising:
a proportioning device;
at least one source of water adapted for operation with the proportioning device;
at least one source of the first concentrate adapted for operation with the proportioning device, wherein the first concentrate includes glucose, is free of potassium ions, and has a pH of 1.5 to 4.5;
at least one source of the second concentrate adapted for operation with the proportioning device, wherein the second concentrate includes a physiologically acceptable buffer and is free of potassium ions; and
at least one source of the third concentrate adapted for operation with the proportioning device, wherein the third concentrate includes a physiologically acceptable buffer and potassium ions, and the potassium ions in the third concentrate have a concentration between 0.04 M and 0.1 M,
wherein the peritoneal dialysis fluid is a dilution of between 1:10 and 1:50 of at least one of the first concentrate, the second concentrate or the third concentrate, and
wherein exclusive of the potassium ions, the third concentrate is the same as the second concentrate.

23. The method of claim 1, wherein both the second concentrate and the third concentrate are free of glucose.

24. The method of claim 23, wherein the first concentrate is free of sodium.

* * * * *